(12) United States Patent
Bernhard et al.

(10) Patent No.: US 11,849,761 B2
(45) Date of Patent: Dec. 26, 2023

(54) CARTRIDGE ASSEMBLY WITH ACTIVATING PIERCING MEMBERS FOR AN AEROSOL-GENERATING SYSTEM

(71) Applicant: PHILIP MORRIS PRODUCTS S.A., Neuchatel (CH)

(72) Inventors: Philipp Bernhard, Thun (CH); Antonino Lanci, Bern (CH); Hannes Merz, Olten (CH); Patrick Charles Silvestrini, Neuchatel (CH); Irene Taurino, Lausanne (CH); Ihar Nikolaevich Zinovik, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 580 days.

(21) Appl. No.: 17/057,881

(22) PCT Filed: Jun. 4, 2019

(86) PCT No.: PCT/EP2019/064542
§ 371 (c)(1),
(2) Date: Nov. 23, 2020

(87) PCT Pub. No.: WO2019/234055
PCT Pub. Date: Dec. 12, 2019

(65) Prior Publication Data
US 2021/0204599 A1 Jul. 8, 2021

(30) Foreign Application Priority Data
Jun. 5, 2018 (EP) .................................. 18176148

(51) Int. Cl.
*A24F 40/30* (2020.01)
*A24F 40/42* (2020.01)
(Continued)

(52) U.S. Cl.
CPC ................. *A24F 40/30* (2020.01); *A24F 7/00* (2013.01); *A24F 40/42* (2020.01); *A24F 40/48* (2020.01);
(Continued)

(58) Field of Classification Search
CPC .. A24F 40/30; A24F 7/00; A24F 40/42; A24F 40/48; A24F 40/10; A24F 40/465;
(Continued)

(56) References Cited

U.S. PATENT DOCUMENTS 10,098,381 B2 * 10/2018 Kane ..................... A24F 40/485
10,258,087 B2 * 4/2019 Kane ................... H05B 3/0014
(Continued)

FOREIGN PATENT DOCUMENTS

CA 2949326 12/2015
EP 2 946 679 11/2015
(Continued)

OTHER PUBLICATIONS

Search Report and Written Opinion for PCT/EP2019/064542 dated Sep. 6, 2019.
(Continued)

*Primary Examiner* — Jean F Duverne
(74) *Attorney, Agent, or Firm* — Mueting Raasch Group

(57) ABSTRACT

There is provided a cartridge assembly (10) for use in an aerosol-generating system, the cartridge assembly comprising: a cartridge (12) comprising at least a first compartment (18) extending along a longitudinal axis, the first compartment comprising an aerosol-generating compound and being sealed at a first end by a first frangible barrier (22) extending in respective planes transverse to the longitudinal axis; and at least a first piercing member (38) configured to rupture the first frangible barrier (22). The first piercing member (38) comprises: a first piercing body (40) having a cross-sectional
(Continued)

surface area at least about 40 percent of a cross-sectional area of the at least one compartment (19); and a first channel (381, 382) extending parallel to the longitudinal axis of the cartridge through the first piercing body (40), the first channel (381, 382) having an inlet and an outlet. The first piercing member (38) is movable along the longitudinal axis from a first position to a second position, wherein, when the first piercing member (38) is in the first position, the first piercing body (40) is retracted from the plane of the first frangible barrier (22); and wherein, when the first piercing member (38) is in the second position, the first piercing body (40) extends into the at least one compartment (18) through the plane of the first frangible barrier (22), and the at least one compartment (18) is in fluid communication with the inlet and outlet of the first channel (281, 382). The at least one compartment (18) is sealed at an end opposite the first end by a second frangible barrier (26), the cartridge assembly (10) further comprising a second piercing member (44) configured to rupture the second frangible barrier (26).

13 Claims, 2 Drawing Sheets

(51) Int. Cl.
*A24F 40/48* (2020.01)
*A24F 7/00* (2006.01)
*H05B 6/10* (2006.01)
*A24F 40/10* (2020.01)
*A24F 40/465* (2020.01)

(52) U.S. Cl.
CPC .............. *H05B 6/105* (2013.01); *A24F 40/10* (2020.01); *A24F 40/465* (2020.01)

(58) Field of Classification Search
CPC .... A24F 40/485; H05B 6/105; A61M 16/107; A61M 2205/8206; A61M 15/0035; A61M 15/0041; A61M 15/06; A61M 11/042; A61M 15/0021; A24B 15/167; A24B 15/243; A24B 15/30
See application file for complete search history.

(56) References Cited

U.S. PATENT DOCUMENTS

| | | | |
|---|---|---|---|
| 2016/0000147 | A1 | 1/2016 | Li |
| 2016/0295917 | A1 | 10/2016 | Malgat |
| 2017/0340003 | A1* | 11/2017 | Batista .................... A24F 40/46 |

FOREIGN PATENT DOCUMENTS

| | | |
|---|---|---|
| EP | 3160274 | 5/2019 |
| WO | WO 2007/143993 | 12/2007 |
| WO | WO 2008/121610 | 10/2008 |
| WO | WO 2014/140320 | 9/2014 |
| WO | WO 2015/197627 | 12/2015 |
| WO | WO 2016/038357 | 3/2016 |
| WO | WO 2016/046362 | 3/2016 |
| WO | WO 2016/156212 | 10/2016 |
| WO | WO 2017/102633 | 6/2017 |
| WO | WO 2019/234055 | 12/2019 |
| WO | WO 2019/243545 | 12/2019 |
| WO | WO 2019/243612 | 12/2019 |

OTHER PUBLICATIONS

Extended European Search Report for Application No. 18176148.7 dated Jan. 2, 2019 (7 pages).
Extended European Search Report for Application No. 22192082.0 dated Mar. 14, 2023 (10 pages).

* cited by examiner

CARTRIDGE ASSEMBLY WITH ACTIVATING PIERCING MEMBERS FOR AN AEROSOL-GENERATING SYSTEM

This application is a U.S. National Stage Application of International Application No. PCT/EP2019/064542 filed Jun. 4, 2019, which was published in English on Dec. 12, 2019 as International Publication No. WO 2019/234055 A1. International Application No. PCT/EP2019/064542 claims priority to European Application No. 18176148.7 filed Jun. 5, 2018.

The present invention relates to a cartridge assembly for use in an aerosol-generating system and to an aerosol-generating system comprising the cartridge assembly. The present invention finds particular application as a cartridge assembly comprising a nicotine source and an acid source for the generation of an aerosol comprising nicotine salt particles.

Devices for delivering nicotine to a user comprising a nicotine source and a delivery enhancing compound source are known. For example, WO 2008/121610 A1 discloses devices in which nicotine and a volatile acid, such as pyruvic acid, are reacted with one another in the gas phase to form an aerosol of nicotine salt particles that can be inhaled by a user.

Differences between the vapour concentrations of nicotine and the volatile delivery enhancing compound in such devices may disadvantageously lead to an unfavourable reaction stoichiometry or the delivery of excess reactant, such as unreacted nicotine vapour or unreacted volatile delivery enhancing compound vapour to a user. The vapour pressure of pyruvic acid at ambient temperature is substantially greater than that of nicotine. Consequently, to balance the concentration of pyruvic acid vapour and nicotine vapour to yield an efficient reaction stoichiometry, it may be necessary to heat the nicotine source and the pyruvic acid source of devices disclosed in WO 2008/121610 A1 to different temperatures. Specifically, it may be necessary to heat the nicotine source to a higher temperature than the pyruvic acid source in order to generate a sufficient or consistent quantity of nicotine pyruvate salt particles for delivery to a user. This requires the nicotine source and the pyruvic acid source to be stored and heated in physically separate cartridges or other components within the device.

A solution to this issue has been disclosed in WO 2015/197627 A1, which provides an aerosol-generating system and method in which a single heater heats to substantially the same temperature both a nicotine source and a volatile delivery enhancing compound source, such as a lactic acid source. The reaction stoichiometry between nicotine vapour and lactic acid vapour is controlled by controlling the ratio of the volumetric airflow through a first compartment comprising the nicotine source and a second compartment comprising the lactic acid source. Another example of an aerosol-generating system wherein a nicotine source and a lactic acid source are held in separate compartments heated by a single heater is known from WO 2016/046362 A1.

Both WO 2015/197627 A1 and WO 2016/046362 disclose examples of cartridge assemblies for use in an aerosol-generating system, such assemblies comprising frangible barriers of a sealing material for sealing the cartridge compartments housing the nicotine source and the volatile delivery enhancing compound source. Suitable sealing materials include, by way of example, aluminium foil and high density polyethylene.

Due to size constraints, however, one or more of the openings formed by the piercing members may at times become blocked during use by portions of the sealing material that have been displaced upon piercing the frangible barriers. This may undesirably alter the ratio in which the compounds housed in the compartments of the cartridge are supplied to the consumer. Further, this may at times disadvantageously lead to an unfavourable reaction stoichiometry, such that some unreacted nicotine vapour or unreacted volatile delivery enhancing compound is undesirably delivered to a user.

Thus, it would be desirable to provide an improved cartridge assembly for use in an aerosol-generating system, the cartridge being configured to maintain the compartments of the cartridge in a sealed state prior to use, which may advantageously increase the shelf life of the cartridge assembly, and such that the occurrences of blockages of the air flow path established through the cartridge are reduced with respect to known cartridge assemblies. Further, it would be desirable to provide an aerosol-generating system comprising one such cartridge assembly.

According to an aspect of the present invention, there is provided a cartridge assembly for use in an aerosol-generating system, the cartridge assembly comprising: a cartridge comprising at least a first compartment extending along a longitudinal axis, the first compartment comprising an aerosol-generating compound and being sealed at a first end by a first frangible barrier extending in respective planes transverse to the longitudinal axis; and at least a first piercing member configured to rupture the first frangible barrier. The first piercing member comprises: a first piercing body having a cross-sectional surface area at least about 40 percent of a cross-sectional area of the at least one compartment; and a first channel extending parallel to the longitudinal axis of the cartridge through the first piercing body, the first channel having an inlet and an outlet. The first piercing member is movable along the longitudinal axis from a first position to a second position, wherein, when the first piercing member is in the first position, the first piercing body is retracted from the plane of the first frangible barrier. Further, when the first piercing member is in the second position, the first piercing body extends into the at least one compartment through the plane of the first frangible barrier, and the at least one compartment is in fluid communication with the inlet and outlet of the first channel.

The at least one compartment is sealed at an end opposite the first end by a second frangible barrier. The cartridge assembly further comprises a second piercing member configured to rupture the second frangible barrier. The second piercing member comprises a second piercing body having a cross-sectional surface area at least about 40 percent of a cross-sectional area of the at least one compartment. In addition, the second piercing member comprises a second channel extending parallel to the longitudinal axis of the cartridge through the second piercing body, the second channel having an inlet and an outlet.

The second piercing member is movable along the longitudinal axis from a first position to a second position. Thus, when the second piercing member is in the first position, the second piercing body is retracted from the plane of the second frangible barrier. Further, when the second piercing member is in the second position, the second piercing body extends into the at least one compartment through the plane of the second frangible barrier, and the at least one compartment is in fluid communication with the inlet and outlet of the second channel.

According to another aspect of the present invention, there is provided an aerosol-generating system comprising a cartridge as set out above, and an aerosol-generating device comprising a device cavity configured to receive an upstream end of the cartridge assembly and a heater for heating the first compartment and the second compartment of the cartridge of the cartridge assembly.

It will be appreciated that any features described with reference to one aspect of the present invention are equally applicable to any other aspect of the invention.

As used herein, the term "aerosol-generating device" refers to a device that interacts with an aerosol-generating article to generate an aerosol that is directly inhalable into a user's lungs thorough the user's mouth.

As set out briefly above, a cartridge assembly in accordance with the present invention comprises a compartment extending along a longitudinal axis, the compartment comprising an aerosol-generating compound and being sealed at an end by a frangible barrier extending in a respective plane transverse to the longitudinal axis. Further, the cartridge comprises a piercing member configured to rupture the frangible barrier.

In contrast to known cartridge assemblies for use in an aerosol-generating system, the piercing member comprises a piercing body having a cross-sectional surface area at least about 40 percent of a cross-sectional area of the at least one compartment. Further, the piercing member comprises a channel extending parallel to the longitudinal axis of the cartridge through the piercing body, such that the channel has an inlet and an outlet at longitudinally opposite ends of the piercing body.

The piercing member is movable along the longitudinal axis from a first position to a second position. When the piercing member is in the first position, the piercing body is retracted from the plane of the frangible barrier. When the piercing member is in the second position, the piercing body extends into the at least one compartment through the plane of the frangible barrier, and the compartment is in fluid communication with the inlet and outlet of the first channel. In practice, the channel extending through the piercing body defines an airflow pathway establishing fluid communication between an internal volume of the compartment, wherein the aerosol-generating compound is held, and the outside of the compartment.

It is easy to activate the cartridge by piercing the frangible barrier with the piercing member. The body of the piercing member is configured and sized to push the material forming the frangible barrier radially away from a central longitudinal axis of the cartridge compartment, as and when the piercing member is moved into the second position. Because of this arrangement, the likelihood that the channel defining the airflow pathway may be obstructed by portions of the frangible barrier becoming dislodged or folding back towards the central longitudinal axis of the cartridge compartment is advantageously significantly reduced.

Activation of the cartridge is not reversible, and so it is easy for the consumer to tell whether a given cartridge has been activated or not.

The at least one compartment is also sealed at an end opposite the first end by a second frangible barrier, and the cartridge assembly comprises a second piercing member configured to rupture the second frangible barrier. To this purpose, the second piercing member comprises a second piercing body having a cross-sectional surface area at least about 40 percent of a cross-sectional area of the at least one compartment. Further, the second piercing member comprises a second channel extending parallel to the longitudinal axis of the cartridge through the second piercing body, and the second channel has an inlet and an outlet. The second piercing member is also movable along the longitudinal axis from a first position to a second position. When in the first position, the second piercing member is retracted from the plane of the second frangible barrier. When in the second position, the second piercing body extends into the at least one compartment through the plane of the second frangible barrier, and the at least one compartment is in fluid communication with the inlet and outlet of the second channel.

As with the first piercing body, one such bulky second piercing body is understood to more effectively displace the material of the second frangible barrier away from the longitudinal axis along which the second piercing member moves. This advantageously reduces the likelihood of the material of the second frangible barrier blocking the channel extending through the second piercing member.

As described above, in a cartridge assembly in accordance with the present invention the first piercing body has a cross-sectional surface area at least about 40 percent of a cross-sectional surface of the at least one compartment. Preferably, the first piercing body has a cross-sectional surface area at least about 50 percent of a cross-sectional surface of the at least one compartment. Even more preferably, the first piercing body has a cross-sectional surface area at least about 75 percent of a cross-sectional surface of the at least one compartment. In particularly preferred embodiments, the first piercing body has a cross-sectional surface area at least about 80 percent of a cross-sectional surface of the at least one compartment.

Without wishing to be bound by theory, a bulkier piercing member is understood to displace a greater portion of the material forming the frangible barrier away from the central longitudinal axis of the at least one compartment. At the same time, a greater distance may be established between the periphery of the inlet and outlet of the channel extending through the piercing member and the portion of frangible barrier displaced. Thus, the likelihood that displaced frangible barrier material may occlude the channel is reduced even further or substantially eliminated.

In addition, or as an alternative, the cross-sectional surface area of the first piercing body is less than about 95 percent of the cross-sectional area of the at least one compartment. More preferably, the cross-sectional surface area of the first piercing body is less than about 90 percent of the cross-sectional area of the at least one compartment. By ensuring that a gap is provided between the periphery of the piercing body and the internal surface of the at least one compartment, smooth and easy operation of the piercing member is facilitated.

The width of such gap may be adjusted to accommodate the displaced frangible barrier material. By way of example, the width of the gap may be increased when the thickness of the frangible barrier is increased, or when the flexibility of the frangible barrier is reduced.

Preferably, the cartridge assembly comprises a mouthpiece, the mouthpiece comprising an upstream mouthpiece end wall and a mouthpiece air inlet in the upstream mouthpiece end wall, the mouthpiece air inlet in fluid communication with the inlet and outlet of the channel, wherein the mouthpiece is configured to be movable along the longitudinal axis of the cartridge with the at least one piercing member.

As with the first piercing body, a bulkier second piercing body is understood to more effectively displace the frangible barrier material away from the longitudinal axis along which the second piercing member moves, which results in a reduce likelihood of blocking of the channel extending through the second piercing member. Thus, the second piercing body preferably has a cross-sectional surface area at least about 50 percent of a cross-sectional surface of the at least one compartment. Even more preferably, the second piercing body has a cross-sectional surface area at least about 75 percent of a cross-sectional surface of the at least one compartment. In particularly preferred embodiments, the second piercing body has a cross-sectional surface area at least about 80 percent of a cross-sectional surface of the at least one compartment. In addition, or as an alternative, the second piercing body preferably has a cross-sectional surface area of less than about 95 percent of a cross-sectional surface of the at least one compartment, even more preferably less than about 90 percent of a cross-sectional surface of the at least one compartment.

The first piercing member and the second piercing member are configured to move along the longitudinal axis in opposite directions. In other words, when moving from the first position to the second position, the first (second) piercing member moves towards the second (first) piercing member. Because, as they move from the first position to the second position, the piercing members at least partly penetrate a compartment of the cartridge, an overall length of the cartridge assembly in the activated state (that is, when both piercing members are in their respective second positions) is less than an overall length of the cartridge assembly in a non-activated state (that is, when both piercing members are in their respective first positions).

In preferred embodiments, the cartridge comprises a second compartment arranged in parallel to the first compartment within the cartridge. This enables two distinct aerosol-forming compounds (as will be described in greater detail below) to be stored and heated in their respective compartments in a single component of an aerosol-generating system. This is advantageous in that it reduces the complexity and cost of manufacturing the aerosol-generating system and the cartridge assembly according to the present invention compared with prior art devices in which the nicotine source and the volatile delivery enhancing compound source are stored and heated in physically separate components within the device.

Further, in such preferred embodiments the first piercing member comprises a third piercing body, the first piercing body being configured to be movable to be at least partly received within the first compartment of the cartridge, and the third piercing body being configured to be movable with the first piercing body to be at least partly received within the second compartment of the cartridge.

In such embodiments, the third piercing body has a cross-sectional surface area at least about 40 percent of a cross-sectional area of the second compartment, the first piercing member further comprising a third channel extending parallel to the longitudinal axis of the cartridge through the third piercing body, the third channel having an inlet and an outlet. As with the first and second piercing bodies, a greater cross-sectional surface area is preferred for the same reasons. Thus, the third piercing body preferably has a cross-sectional surface area at least about 50 percent of a cross-sectional surface of the second compartment. Even more preferably, the third piercing body has a cross-sectional surface area at least about 75 percent of a cross-sectional surface of the second compartment. In particularly preferred embodiments, the third piercing body has a cross-sectional surface area at least about 80 percent of a cross-sectional surface of the second compartment. In addition, or as an alternative, the third piercing body preferably has a cross-sectional surface area of less than about 95 percent of a cross-sectional surface of the second compartment, even more preferably less than about 90 percent of a cross-sectional surface of the second compartment.

Because the first piercing body and the third piercing body move together as two portions of the same first piercing member, the sealing barrier at one end of the cartridge can advantageously be pierced at locations corresponding to both first and second compartments at the same time. Thus, an airflow pathway is established at once into both compartments, such that the two aerosol-forming components can be delivered to the user in combination.

Even more preferably, the second piercing member comprises a fourth piercing body, the second piercing body being configured to be movable to be at least partly received within the first compartment of the cartridge, and the fourth piercing body being configured to be movable with the second piercing body to be at least partly received within the second compartment of the cartridge.

The fourth piercing body has a cross-sectional surface area at least about 40 percent of a cross-sectional area of the second compartment, the second piercing member further comprising a fourth channel extending parallel to the longitudinal axis of the cartridge through the fourth piercing body, the fourth channel having an inlet and an outlet. As with the first, second and third piercing bodies, a greater cross-sectional surface area is preferred for the same reasons. Thus, the fourth piercing body preferably has a cross-sectional surface area at least about 50 percent of a cross-sectional surface of the second compartment. Even more preferably, the fourth piercing body has a cross-sectional surface area at least about 75 percent of a cross-sectional surface of the second compartment. In particularly preferred embodiments, the fourth piercing body has a cross-sectional surface area at least about 80 percent of a cross-sectional surface of the second compartment. In addition, or as an alternative, the fourth piercing body preferably has a cross-sectional surface area of less than about 95 percent of a cross-sectional surface of the second compartment, even more preferably less than about 90 percent of a cross-sectional surface of the second compartment.

Because the second piercing body and the fourth piercing body move together as two portions of the same second piercing member, the sealing barrier at the other end of the cartridge can advantageously be pierced at locations corresponding to both first and second compartments at the same time. Thus, an airflow pathway is established at once into both compartments, such that air can be drawn into the compartments holding the two aerosol-forming components simultaneously for them to be delivered to the user in combination.

In preferred embodiments, the cartridge comprises a first compartment and a second compartment, a nicotine source being positioned within the first compartment and an acid source being positioned within the second compartment. The nicotine source may comprise one or more of nicotine, nicotine base, a nicotine salt, such as nicotine-HCl, nicotine-bitartrate, or nicotine-ditartrate, or a nicotine derivative. The nicotine source may comprise natural nicotine or synthetic nicotine. The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulphate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The nicotine source may comprise a sorption element and nicotine sorbed on the sorption element.

The sorption element may be formed from any suitable material or combination of materials. For example, the sorption element may comprise one or more of glass, cellulose, ceramic, stainless steel, aluminium, polyethylene (PE), polypropylene, polyethylene terephthalate (PET), poly (cyclohexanedimethylene terephthalate) (PCT), polybutylene terephthalate (PBT), polytetrafluoroethylene (PTFE), expanded polytetrafluoroethylene (ePTFE), and BAREX®.

The sorption element may be a porous sorption element. For example, the sorption element may be a porous sorption element comprising one or more materials selected from the group consisting of porous plastic materials, porous polymer fibres and porous glass fibres.

The sorption element is preferably chemically inert with respect to nicotine. The sorption element may have any suitable size and shape.

Preferably, the acid source is a lactic acid source. The lactic acid source may comprise a sorption element and lactic acid sorbed on the sorption element.

The sorption element may be formed from any suitable material or combination of materials, for example those listed above.

The sorption element is preferably chemically inert with respect to lactic acid. The sorption element may have any suitable size and shape.

In certain embodiments the sorption element may be a substantially cylindrical plug. For example, the sorption element may be a porous substantially cylindrical plug. In other embodiments the sorption element may be a substantially cylindrical hollow tube. For example, the sorption element may be a porous substantially cylindrical hollow tube.

In other embodiments the sorption element may be a substantially parallelepiped plug. For example, the sorption element may be a porous substantially parallelepiped plug. A cross-section of the plug may be substantially square- or rectangular-shaped. In other embodiments, the sorption element may be a substantially parallelepiped hollow tubular element. For example, the sorption element may be a porous substantially parallelepiped hollow tubular element with a rectangular cross-section.

The size, shape and composition of the sorption element may be chosen to allow a desired amount of lactic acid to be sorbed on the sorption element. The sorption element advantageously acts as a reservoir for the lactic acid.

Preferably, the cartridge assembly is configured such that the reaction stoichiometry between nicotine vapour and lactic acid vapour is balanced and controlled by the ratio of volumetric air flow through the first compartment and the second compartment. In more detail, the ratio of the volumetric airflow through the first compartment relative to the volumetric airflow through the second compartment is preferably controlled through variation of one or both of the number and dimensions of air inlets in communication with the first compartment relative to the number and dimensions of air inlets in communication with the second compartment.

In preferred embodiments, the ratio of the volumetric airflow through the first compartment relative to the volumetric airflow through the second compartment is controlled by having a different number of equally sized air inlets in communication with the first compartment and the second compartment, respectively.

In general, in cartridge assemblies in accordance with the present invention, air inlets into and out of the first compartment and the second compartment are defined by the channel or channels extending through the piercing bodies of the piercing members. Thus, in order to achieve a desirable 1:1 stoichiometry between nicotine and lactic acid, in preferred embodiments of the cartridge assemblies in accordance with the present invention, the third and fourth piercing bodies (that is, the ones operatively coupled with the compartment containing the lactic acid source) preferably comprise twice as many channels as the first and third piercing bodies (that is, the ones operatively coupled with the compartment containing the nicotine source). In a particularly preferred embodiment, the first and third piercing bodies comprise two channels each, and the second and fourth piercing bodies comprise four channels each.

In those embodiments comprising a mouthpiece as described above, the mouthpiece preferably comprises a mouthpiece chamber positioned downstream of the upstream mouthpiece end wall and in fluid communication with the mouthpiece air inlet. Further, the mouthpiece preferably further comprises a mouthpiece air outlet at a downstream end of the mouthpiece chamber.

In such embodiments, the mouthpiece preferably further comprises a ventilation air inlet providing fluid communication between the exterior of the mouthpiece and the mouthpiece chamber, wherein the ventilation air inlet is position between the upstream mouthpiece end wall and the downstream end of the mouthpiece chamber.

Further, where the cartridge assembly comprises a mouthpiece, the mouthpiece may comprise a filter. The filter may have a low particulate filtration efficiency or very low particulate filtration efficiency.

In some preferred embodiments, the cartridge assembly further comprises a third compartment for receiving a heating element of an aerosol-generating device, the third compartment positioned between the first compartment and the second compartment, and wherein the upstream housing end wall comprises an aperture aligned with the third compartment when the cartridge is in the second position.

Heating the nicotine source and the lactic acid source to a temperature above ambient temperature using a single heater allows control of the amount of nicotine vapour and lactic acid vapour released from the nicotine source and the lactic acid source, respectively. This advantageously enables the vapour concentrations of the nicotine and the lactic acid to be controlled and balanced proportionally to yield an efficient reaction stoichiometry. This advantageously improves the efficiency of the formation of an aerosol and the consistency of nicotine delivery to a user. Further, it advantageously reduces the risk of undesired delivery of excess reactant, that is unreacted nicotine vapour or unreacted lactic acid vapour, to a user.

Preferably, the heating element is provided as a susceptor positioned between the first compartment and the second compartment. This makes it possible for the heating of the aerosol-forming components in the cartridge assembly to be effected in a contactless manner by induction-heating.

To this purpose, one such cartridge assembly according to the present invention is used in an aerosol-generating device comprising an induction source, which is configured to produce an alternating electromagnetic field that induces a heat generating eddy current in the susceptor material.

The susceptor is arranged in thermal proximity of the aerosol-forming components in the compartments of the cartridge assembly. The heated susceptor in turn heats the aerosol-forming components to release volatile compounds and form an aerosol.

The susceptor comprises a first susceptor material and a second susceptor material, the first susceptor material being disposed in intimate physical contact with the second susceptor material. The second susceptor material preferably has a Curie temperature that is lower than 500 degrees Celsius. The first susceptor material is preferably used primarily to heat the susceptor when the susceptor is placed in a fluctuating electromagnetic field. Any suitable material may be used. For example the first susceptor material may be aluminium, or may be a ferrous material such as a stainless steel. The second susceptor material is preferably used primarily to indicate when the susceptor has reached a specific temperature, that temperature being the Curie temperature of the second susceptor material. The Curie temperature of the second susceptor material can be used to regulate the temperature of the entire susceptor during operation. Thus, the Curie temperature of the second susceptor material should be below the ignition point of the aerosol-forming substrate. Suitable materials for the second susceptor material may include nickel and certain nickel alloys.

The invention will now be further described with reference to the drawings of the following Figures, wherein.

Figure 1:
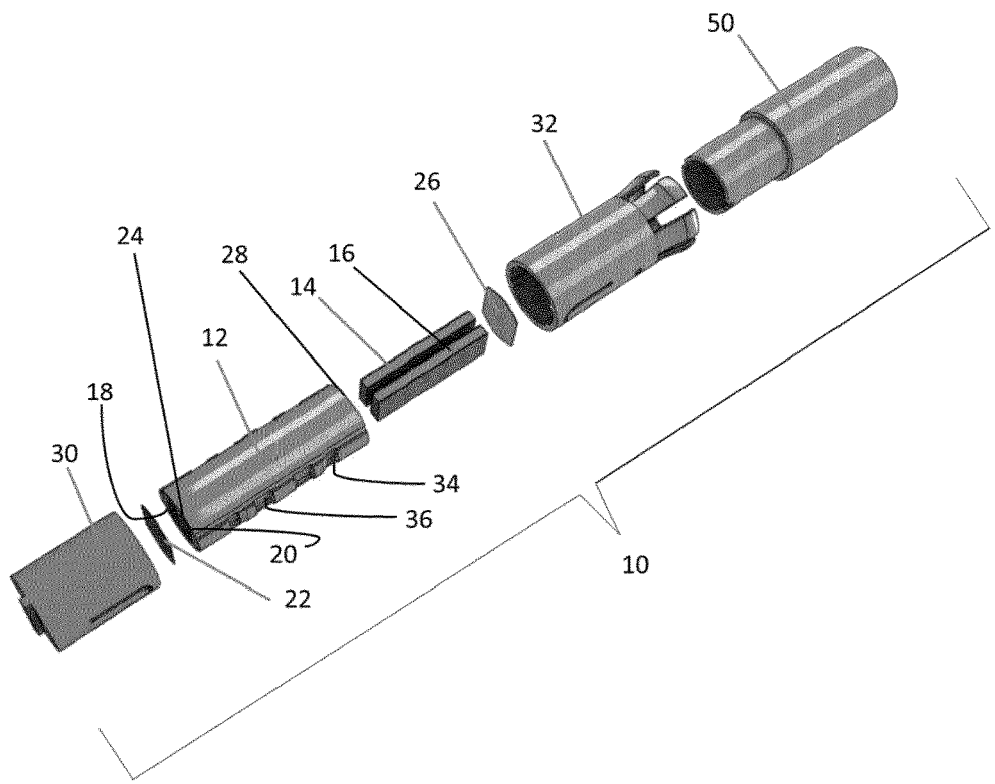
FIG. 1 is an exploded perspective view of a cartridge assembly in accordance with the present invention.
Figure 2:
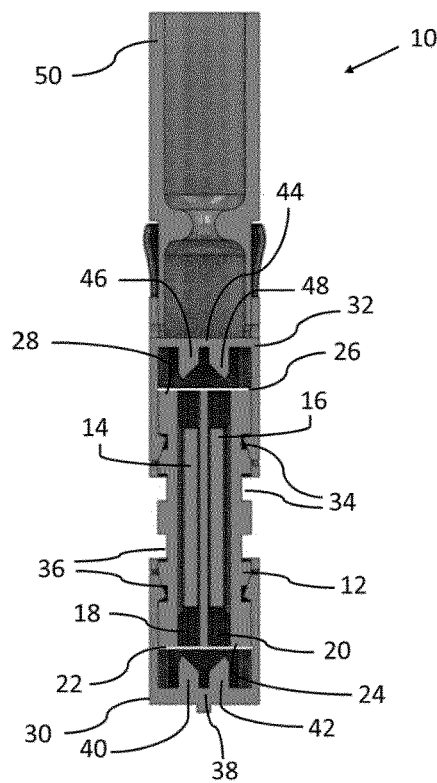
FIG. 2 is a side, sectional view of the cartridge assembly of FIG. 1 with the piercing members in their respective first, retracted positions.
Figure 3:
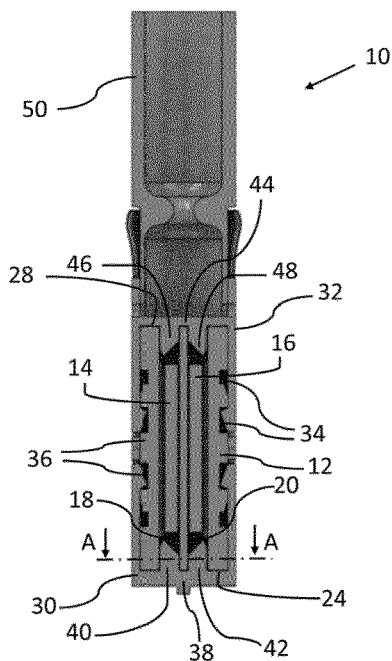
FIG. 3 is a further side, sectional view of the cartridge assembly of FIGS. 1 and 2 with the piercing members in their respective second positions (activated cartridge)

The cartridge assembly 10 in FIGS. 1, 2 and 3 comprises a substantially cylindrical cartridge 12 adapted to receive a pair of sorption elements 14, 16 into respective first and second compartments 18, 20. The first sorption element 14 is loaded with a nicotine source, whereas the second sorption element 16 is loaded with a lactic acid source. Both compartments 18, 20 are sealed at their ends by a first frangible barrier 22 provided at an upstream end 24 of the cartridge 12 and a second frangible barrier 26 provided at a downstream end 28 of the cartridge 12.

Further, the cartridge assembly 10 comprises an upstream shell member 30 and a downstream shell member 32. The upstream shell member 30 and the downstream shell member 32 are adapted to be fitted onto the cartridge 12. Each one of the shell members 30, 32 comprises a tubular body adapted to partly receive the cartridge 12. In more detail, in the embodiment shown in FIGS. 1, 2 and 3, each one of the tubular bodies of the shell members 30, 32 has a length such as to be able to accommodate about 50 percent of the length of the cartridge.

The shell members 30, 32 comprise retaining elements adapted to snap-fit into corresponding slits or grooves in a lateral wall of the cartridge 12. In more detail, the lateral wall of the cartridge comprises two pairs 34, 36 of slits or grooves, such that each one of the shell members 30, 32 can snap-fit onto the cartridge in a first position (see FIG. 2), wherein the shell members 30, 32 are at a distance from one another, and in a second position (see FIG. 3), wherein the shell members are substantially in abutting relationship. The shell members 30, 32 are thus movable longitudinally from the first position to the second position.

The upstream shell member 30 comprises a first piercing member 38 configured to rupture the first frangible barrier 22. The first piercing member 38 comprises a first piercing body 40 and a second piercing body 42. The first piercing member 38 is movable as part of the upstream shell member 28 from the first position to the second position. When in the first position (see FIG. 2), the first piercing member 38 is retracted from the plane of the first frangible barrier 22. When in the second position (see FIG. 3), the first and second piercing bodies 40, 42 of the first piercing member 38 extend into the first and second compartments 18, 20, respectively.

Each one of the first and second piercing bodies 40, 42 has a cross-sectional surface area of about 90 percent of a cross-sectional area of the respective compartment 18 or 20.

Further, the first piercing member 38 comprises two channels 381, 382 (see FIG. 4) extending parallel to the longitudinal axis of the cartridge through the first piercing body 40 and four channels 383, 384, 385, 386 extending parallel to the longitudinal axis of the cartridge through the second piercing body 42. Such channels have respective inlets and outlets.

Thus, when the first and second piercing bodies 40, 42 are in the second position (see FIG. 3), the first and second compartments 18, 20 are independently in fluid communication with the inlets and outlets of the channels extending through their respective piercing bodies 40, 42.

The downstream shell member 32 comprises a second piercing member 44 configured to rupture the second frangible barrier 26. The second piercing member 44 comprises a third piercing body 46 and a fourth piercing body 48. The second piercing member 44 is movable as part of the downstream shell member 32 from the first position to the second position. When in the first position (see FIG. 2), the second piercing member 44 is retracted from the plane of the second frangible barrier 26. When in the second position (see FIG. 3), the third and fourth piercing bodies 46, 48 of the second piercing member 44 extend into the first and second compartments 18, 20, respectively.

Each one of the third and fourth piercing bodies 46, 48 has a cross-sectional surface area of about 90 percent of a cross-sectional area of the respective compartment 18 or 20.

Further, the second piercing member 44 comprises two channels extending parallel to the longitudinal axis of the cartridge through the third piercing body 46 and four channels extending parallel to the longitudinal axis of the cartridge through the second piercing body 48. Such channels have respective inlets and outlets.

Thus, when the third and fourth piercing bodies 46, 48 are in the second position (see FIG. 3), the first and second compartments 18, 20 are independently in fluid communication with the inlets and outlets of the channels extending through their respective piercing bodies 46, 48.

The cartridge assembly 10 further comprises a mouthpiece 50 detachably attached to a downstream end of the downstream shell member 32. As such, the mouthpiece 50 is configured to be movable along the longitudinal axis of the cartridge 12 with the first one piercing member 38. The mouthpiece 50 comprises an upstream mouthpiece end wall 52 and a mouthpiece air inlet 54 in the upstream mouthpiece end wall 52. The mouthpiece air inlet 54 is in fluid communication with the inlet and outlet of the channels of the first piercing member 38.

Further, the mouthpiece 50 comprises a mouthpiece chamber 56 positioned downstream of the upstream mouthpiece end wall 52 and in fluid communication with the mouthpiece air inlet 54. The mouthpiece 50 further comprises a mouthpiece air outlet 58 at a downstream end 60 of the mouthpiece chamber 56.

In the embodiment of the Figures, the mouthpiece 50 further comprises a ventilation air inlet 62 providing fluid communication between the exterior of the mouthpiece 50 and the mouthpiece chamber 56. In more detail, the ventilation air inlet 62 is positioned between the upstream mouthpiece end wall 52 and the downstream end 60 of the mouthpiece chamber 56.

In order to use the cartridge assembly 10 in an aerosol-generating device, the consumer activates the cartridge by moving the piercing members 38, 44 from the first position into the second position, such that the frangible barriers 22, 26 are ruptured and the compartments 18, 20 are placed in fluid communication with the mouthpiece and the outer environment.

Figure 4:
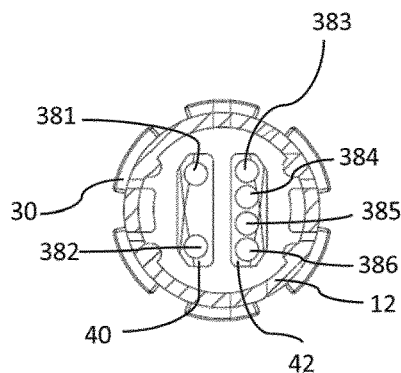
FIG. 4 is a schematic cross-sectional view of the cartridge assembly in the plane A-A of FIG. 3.
Figure 5:
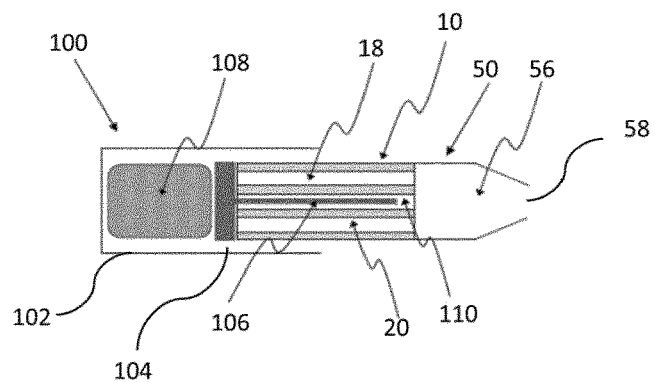
FIG. 5 is a schematic sectional side view of an aerosol-generating device comprising the cartridge assembly of FIGS. 1 to 4.

As shown schematically in FIG. 5, the aerosol-generating device 100 comprises a housing 102 comprising a substantially cylindrical cavity 104 in which the cartridge assembly 10 is partly received. As shown in FIG. 4, the length of the cavity 104 is less than the length of the cartridge assembly 10 so that when the cartridge assembly 10 is inserted into the aerosol-generating device 100 at least the mouthpiece 50 projects from the cavity 104.

The aerosol-generating device 100 comprises heating means configured to heat the compartments 18, 20 of the cartridge assembly. In the embodiment schematically represented in FIG. 4, the aerosol-generating device 100 comprises a heater 106 positioned centrally within the cavity 104 and extending along the major axis of the cavity. The heater is an elongate electric heating element in the form of a heater blade. The aerosol-generating device further comprises a power supply 108 in the form of a battery and a controller (not shown) comprising electronic circuitry, which is connected to the power supply 108 and to the heater 106.

As shown in FIG. 4, the heater is received in a cavity 110 of the cartridge assembly 10 extending centrally between the compartments 18, 20. Once the cartridge assembly is inserted into the aerosol-generating device 100 and activated as set out above, the heater 106 heats the nicotine source and the lactic acid source in the cartridge 12 to substantially the same temperature of about 100 degrees Celsius.

During use, the consumer draws on the mouthpiece 50 of the cartridge assembly 10 to draw air through the cartridge 12. As the drawn air passes through the cartridge 12, nicotine vapour is released from the nicotine source in the first compartment 18 and lactic acid vapour is released from the lactic acid source in the second compartment 20. The nicotine vapour reacts with the lactic acid vapour in the gas phase to form an aerosol of nicotine lactate salt particles, which is delivered to the consumer through the mouthpiece chamber 56 and the mouthpiece air outlet 58.

The invention claimed is:

1. A cartridge assembly for use in an aerosol-generating system, the cartridge assembly comprising:
    a cartridge comprising at least a first compartment extending along a longitudinal axis, the first compartment comprising an aerosol-generating compound and being sealed at a first end by a first frangible barrier extending in respective planes transverse to the longitudinal axis;
    at least a first piercing member configured to rupture the first frangible barrier;
    wherein the first piercing member comprises:
    a first piercing body having a cross-sectional surface area at least about 40 percent of a cross-sectional surface area of the at least one compartment; and
    a first channel extending parallel to the longitudinal axis of the cartridge through the first piercing body, the first channel having an inlet and an outlet;
    the first piercing member being movable along the longitudinal axis from a first position to a second position,
    wherein, when the first piercing member is in the first position, the first piercing body is retracted from the plane of the first frangible barrier; and
    wherein, when the first piercing member is in the second position, the first piercing body extends into the at least one compartment through the plane of the first frangible barrier, and the at least one compartment is in fluid communication with the inlet and outlet of the first channel;
    wherein the at least one compartment is sealed at an end opposite the first end by a second frangible barrier, the cartridge assembly further comprising a second piercing member configured to rupture the second frangible barrier; wherein the second piercing member comprises:
    a second piercing body having a cross-sectional surface area at least about 40 percent of a cross-sectional area of the at least one compartment; and
    a second channel extending parallel to the longitudinal axis of the cartridge through the second piercing body, the second channel having an inlet and an outlet;
    the second piercing member being movable along the longitudinal axis from a first position to a second position, wherein, when the second piercing member is in the first position, the second piercing body is retracted from the plane of the second frangible barrier; and
    wherein, when the second piercing member is in the second position, the second piercing body extends into the at least one compartment through the plane of the second frangible barrier, and the at least one compartment is in fluid communication with the inlet and outlet of the second channel.

2. A cartridge assembly according to claim 1 wherein the cross-sectional surface area of the first piercing body is at least about 50 percent of the cross-sectional area of the at least one compartment.

3. A cartridge assembly according to claim 1 wherein the cross-sectional surface area of the first piercing body is at least about 75 percent of the cross-sectional area of the at least one compartment.

4. A cartridge assembly according to claim 1 comprising a mouthpiece, the mouthpiece comprising an upstream mouthpiece end wall and a mouthpiece air inlet in the upstream mouthpiece end wall, the mouthpiece air inlet in fluid communication with the inlet and outlet of the channel, wherein the mouthpiece is configured to be movable along the longitudinal axis of the cartridge with the at least one piercing member.

5. A cartridge assembly according to claim 1, wherein the cartridge comprises a second compartment arranged in parallel to the first compartment within the cartridge, wherein the first piercing member further comprises a third piercing body, the first piercing body being configured to be movable to be at least partly received within the first compartment of the cartridge, and the third piercing body being configured to be movable with the first piercing body to be at least partly received within the second compartment of the cartridge.

6. A cartridge assembly according to claim 5, wherein the third piercing body has a cross-sectional surface area at least about 40 percent of a cross-sectional area of the second compartment, the first piercing member further comprising a third channel extending parallel to the longitudinal axis of the cartridge through the third piercing body, the third channel having an inlet and an outlet.

7. A cartridge assembly according to claim 4, wherein the mouthpiece comprises a mouthpiece chamber positioned downstream of the upstream mouthpiece end wall and in fluid communication with the mouthpiece air inlet, and wherein the mouthpiece further comprises a mouthpiece air outlet at a downstream end of the mouthpiece chamber.

8. A cartridge assembly according to claim 7, wherein the mouthpiece further comprises a ventilation air inlet providing fluid communication between the exterior of the mouthpiece and the mouthpiece chamber, wherein the ventilation air inlet is positioned between the upstream mouthpiece end wall and the downstream end of the mouthpiece chamber.

9. A cartridge assembly according to claim 1, wherein the cartridge further comprises a second compartment, a nicotine source positioned within the first compartment and an acid source positioned within the second compartment.

10. A cartridge assembly according to claim 1, wherein the cartridge further comprises a third compartment for receiving a heating element of an aerosol-generating device, the third compartment positioned between the first compartment and the second compartment, and wherein the upstream housing end wall comprises an aperture aligned with the third compartment when the cartridge is in the second position.

11. A cartridge assembly according to claim 9, wherein the cartridge comprises a susceptor positioned between the first compartment and the second compartment.

12. An aerosol-generating system comprising:
a cartridge assembly according claim 1; and
an aerosol-generating device comprising a device cavity configured to receive an upstream end of the cartridge assembly and a heater for heating the first compartment and the second compartment of the cartridge of the cartridge assembly.

13. An aerosol-generating system according to claim 12, wherein the heater comprises an inductive heater surrounding at least a portion of the device cavity, and wherein the cartridge comprises a susceptor positioned between the first compartment and the second compartment.

* * * * *